(12) United States Patent
Ishiyama

(10) Patent No.: US 9,561,007 B2
(45) Date of Patent: Feb. 7, 2017

(54) X-RAY DIAGNOSTIC APPARATUS

(71) Applicant: Toshiba Medical Systems Corporation, Otawara-shi (JP)

(72) Inventor: Fumio Ishiyama, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 317 days.

(21) Appl. No.: 14/022,900

(22) Filed: Sep. 10, 2013

(65) Prior Publication Data

US 2014/0010345 A1 Jan. 9, 2014

Related U.S. Application Data

(63) Continuation-in-part of application No. PCT/JP2013/003453, filed on May 31, 2013.

(30) Foreign Application Priority Data

Jun. 28, 2012 (JP) ................................. 2012-145250

(51) Int. Cl.
*A61B 6/00* (2006.01)
*A61B 6/02* (2006.01)
*H05G 1/70* (2006.01)

(52) U.S. Cl.
CPC ............. *A61B 6/022* (2013.01); *A61B 6/4007* (2013.01); *H05G 1/70* (2013.01)

(58) Field of Classification Search
CPC .......... A61B 6/022; A61B 6/4007; H05G 1/70
See application file for complete search history.

(56) References Cited

U.S. PATENT DOCUMENTS

| 4,888,794 A | 12/1989 | Haaker et al. |
| 5,583,345 A | 12/1996 | Kohgami et al. |

(Continued)

FOREIGN PATENT DOCUMENTS

| CN | 1514300 A | 7/2004 |
| JP | 63-261472 A | 10/1988 |

(Continued)

OTHER PUBLICATIONS

Combined Chinese Office Action and Search Report issued May 19, 2015 in Patent Application No. 201380000808.3 (with partial English language translation).

(Continued)

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

To provide an X-ray diagnostic apparatus capable of providing a stereoscopic perspective image in the form of a video image while reducing exposure dose. An X-ray diagnosis apparatus according to an embodiment includes: a main row X-ray source group including a plurality of X-ray sources; an X-ray detection section disposed opposite to the X-ray sources; a timing controller that controls a switching timing of the X-ray sources and an X-ray generation position; an image acquisition section that acquires output image data from the X-ray detection section in synchronization with the switching timing; and a stereoscopic image display section that displays the output image data as a plurality of images having different disparities.

12 Claims, 12 Drawing Sheets

(56) References Cited

U.S. PATENT DOCUMENTS

| | | | |
|---|---|---|---|
| 6,416,476 B1 | 7/2002 | Ogasawara et al. | |
| 6,944,263 B2 * | 9/2005 | Xiao | G03C 9/00 378/41 |
| 7,369,641 B2 | 5/2008 | Tsubaki et al. | |
| 7,567,648 B2 | 7/2009 | Tsubaki et al. | |
| 2006/0170674 A1 | 8/2006 | Tsubaki et al. | |
| 2012/0068079 A1 * | 3/2012 | Agano | G01V 5/0058 250/393 |
| 2012/0253200 A1 | 10/2012 | Stolka et al. | |

FOREIGN PATENT DOCUMENTS

| | | |
|---|---|---|
| JP | 07-079961 A | 3/1995 |
| JP | 9-84000 A | 3/1997 |
| JP | 2000-201925 A | 7/2000 |
| JP | 2005-349127 A | 12/2005 |
| JP | 2006-212056 A | 8/2006 |
| JP | 2007-175271 A | 7/2007 |
| JP | 2009-072360 A | 4/2009 |
| JP | 2009-136518 A | 6/2009 |
| JP | 2011/063266 A2 | 5/2011 |

OTHER PUBLICATIONS

International Search Report mailed Jul. 30, 2013 for PCT/JP2013/003453 filed on May 31, 2013 with English Translation of Categories.

International Written Opinion mailed Jul. 30, 2013 for PCT/JP2013/003453 filed on May 31, 2013.

Combined Chinese Office Action and Search Report issued Dec. 23, 2015 in Patent Application No. 201380000808.3 (with English translation of categories of cited documents).

* cited by examiner

X-RAY DIAGNOSTIC APPARATUS

CROSS-REFERENCE TO RELATED APPLICATION

This application is a continuation-in-part of International Application No. PCT/JP2013/003453, filed on May 31, 2013, which is based upon and claims the benefit of priority from the prior Japanese Patent application No. 2012-145250, filed on Jun. 28, 2012, the entire contents of which are incorporated herein by reference.

FIELD

The present invention relates to an X-ray diagnostic apparatus capable of stereoscopic viewing.

BACKGROUND

As a diagnostic apparatus that observes three dimensionally an inside of a body of a subject body by utilizing an X-ray that penetrates a human body, an X-ray CT apparatus, a cardiovascular X-ray diagnostic apparatus, a digital tomosynthesis system, and the like can be taken.

The X-ray CT apparatus uses various tomographic images of the subject to reconstruct a complete 3D structure. However, the X-ray CT apparatus has a rotation mechanism for scanning and is thus not suitable for radiography of a fast moving organ, such as heart. Thus, an attempt is made to increase a scan speed by increasing the number of rows of detector elements and rotating speed. However, a radiography range is still narrow, and a video image of 30 frames per second cannot yet be acquired. At present, even an apparatus providing a high scanning speed can acquire an image of nothing more than 3 frames per second. In addition, the X-ray CT apparatus irradiates the entire circumference of the subject with an X-ray to photograph about 600 to 1,800 X-ray images per one rotation, disadvantageously increasing exposure dose. Further, scanning is performed in a state where a patient is lying on a bed, so that an image cannot be acquired from a patient in a standing position. This poses a problem that correct diagnosis cannot be made for a part at which a position of internal organs or a status of joints is changed by influence of gravity.

The cardiovascular X-ray diagnostic apparatus can acquire a video image of 30 frames per second. Further, the cardiovascular X-ray diagnostic apparatus performs X-ray irradiation from nothing more than two directions at most (double-arm type), so that the exposure dose is lower than that in the X-ray CT apparatus. However, in order to grasp a 3D structure of the subject from two X-ray images obtained by irradiation of different angles, an operator is required to have anatomical knowledge and technical skill.

The digital tomosynthesis system is a system that is obtained by digitizing an X-ray tomography and can synthesize tomographic images of the subject with low exposure dose. However, the digital tomosynthesis system is not suitable for kinetics observation of fast moving organs or joints due to a mechanism of mechanically moving an X-ray source. An object of an embodiment of the present invention is therefore to solve the above problems and to provide an X-ray diagnostic apparatus capable of providing a stereoscopic video image while reducing exposure dose.

DETAILED DESCRIPTION

According to an embodiment of the present invention, there is provided an X-ray diagnosis apparatus according to an embodiment including: a main row X-ray source group including a plurality of X-ray sources; an X-ray detection section disposed opposite to the X-ray sources; a timing controller that controls a switching timing of the X-ray sources and an X-ray generation position; an image acquisition section that acquires output image data from the X-ray detection section in synchronization with the switching timing; and a stereoscopic image display section that displays the output image data as a plurality of images having different disparities.

First Embodiment

Figure 1:
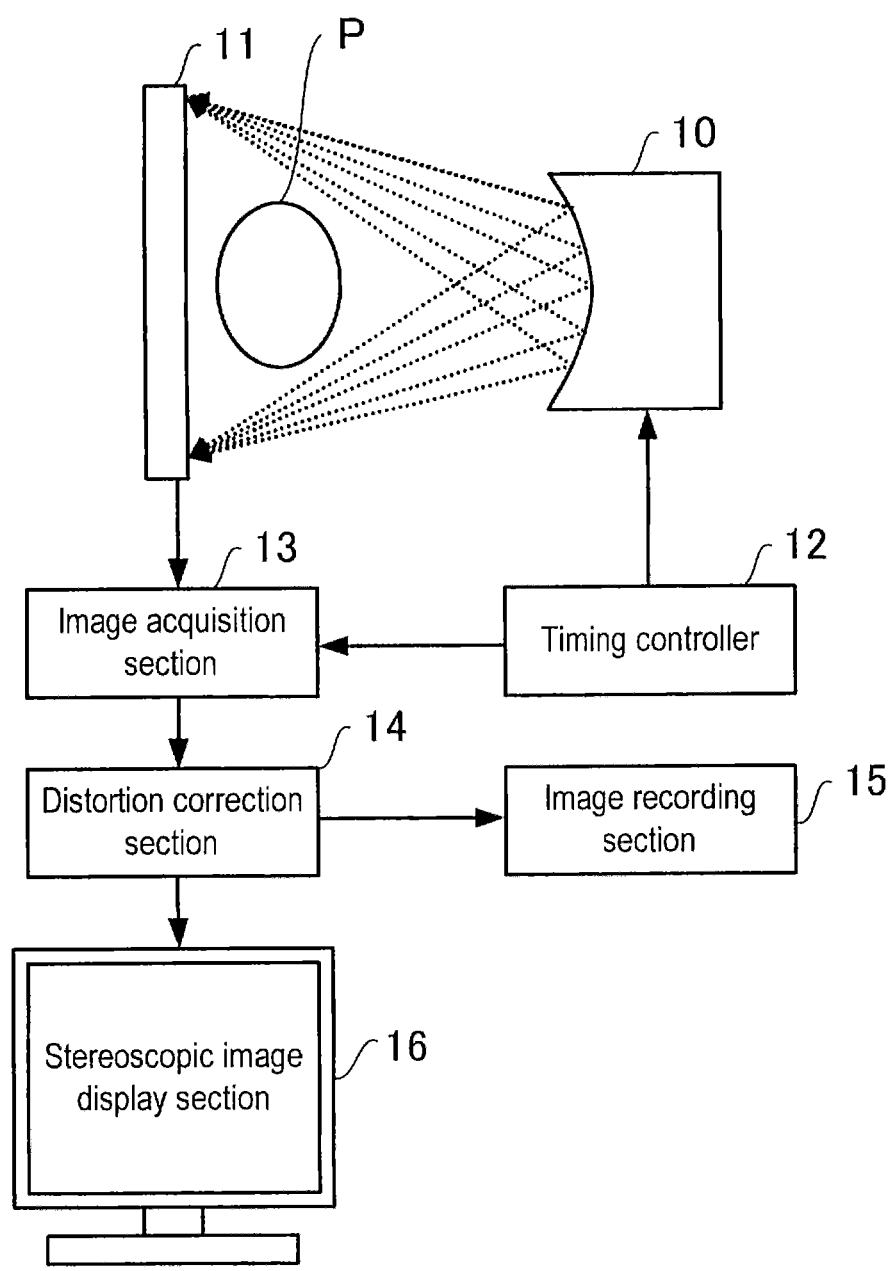
FIG. 1 is a block configuration diagram of an X-ray diagnostic apparatus in a first embodiment.

Embodiments for practicing the present invention will be described in detail below with reference to the accompanying drawings. FIG. 1 is a block configuration diagram of an X-ray diagnostic apparatus 1 in a first embodiment, as viewed from above. The X-ray diagnostic apparatus 1 includes a multi-output X-ray source section 10, an X-ray detection section 11, a timing controller 12, an image acquisition section 13, a distortion correction section 14, an image recording section 15, and a stereoscopic image display section 16.

The multi-output X-ray source section 10 includes a plurality of small X-ray sources and can output X-rays from a plurality of different positions as denoted by dotted arrows. The X-rays of different angles emitted from the multi-output X-ray source section 10 is transmitted through a subject P and then enters the X-ray detection section 11.

Figure 2:
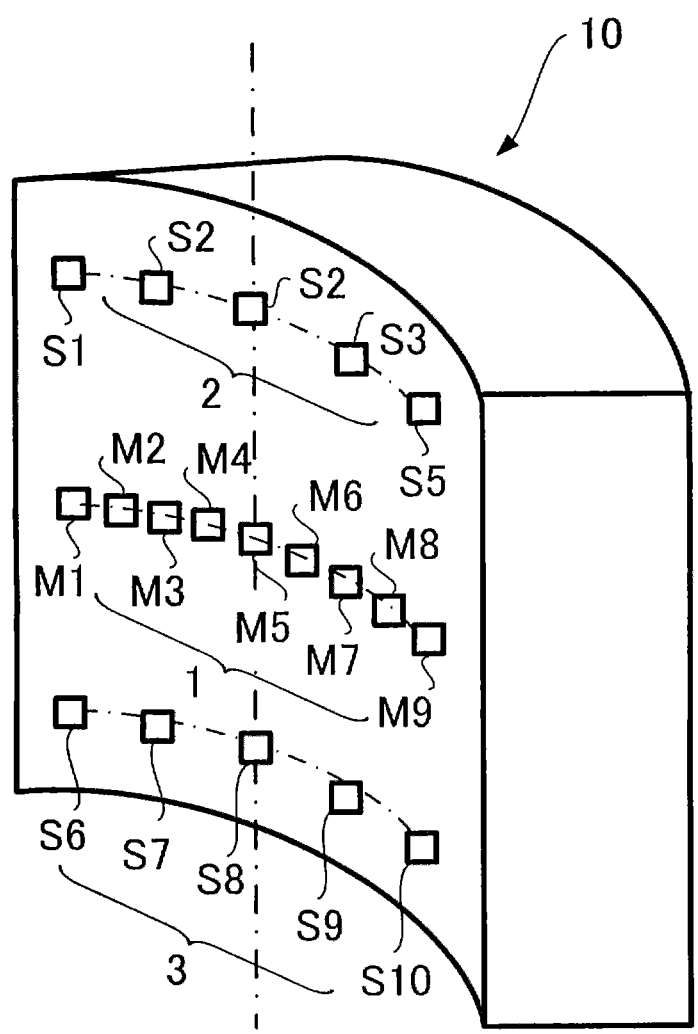
FIG. 2 is a configuration view of a multi-output X-ray source section in the first embodiment.

FIG. 2 is a configuration view of the multi-output X-ray source section 10 of FIG. 1. The multi-output X-ray source section 10 has a plurality of X-ray output ports. In the example of FIG. 2, 19 X-ray output ports are provided. As a main row 1, nine X-ray output ports M1 to M9 are arranged in a central horizontal row of the multi-output X-ray source section 10. Further, as sub rows 2 and 3, five X-ray output ports S1 to S5 and five X-ray output ports S6 to S10 are arranged at upper and lower portions of the multi-output X-ray source section 10, respectively. Shapes of the X-ray output ports M1 to M9 and X-ray output ports S1 to S10 are substantially rectangular and are set such that the entire surface of the X-ray detection section 11 is irradiated. A slit mechanism may be used to make the irradiation area conform to the shape of the X-ray detection section 11.

Figure 3:
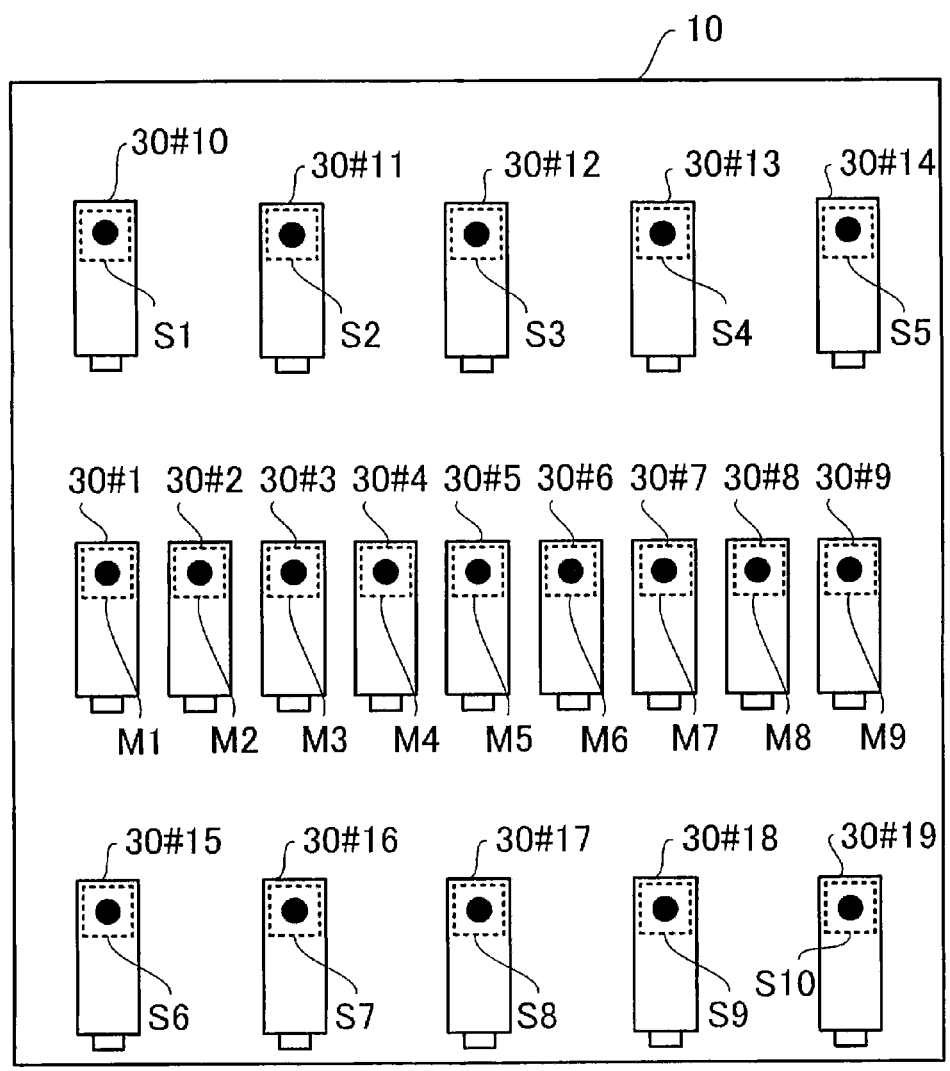
FIG. 3 is a side view illustrating an internal configuration of the multi-output X-ray source section in the first embodiment.

FIG. 3 is a view illustrating an internal configuration of the multi-output X-ray source section 10 as viewed in a direction facing an X-ray output surface thereof. There are arranged small X-ray sources 30#1 to 30#9, 30#10 to 30#14, and 30#15 to 30#19 at positions corresponding to the X-ray output ports of the main row 1, sub row 2, and sub row 3, respectively.

Figure 4:
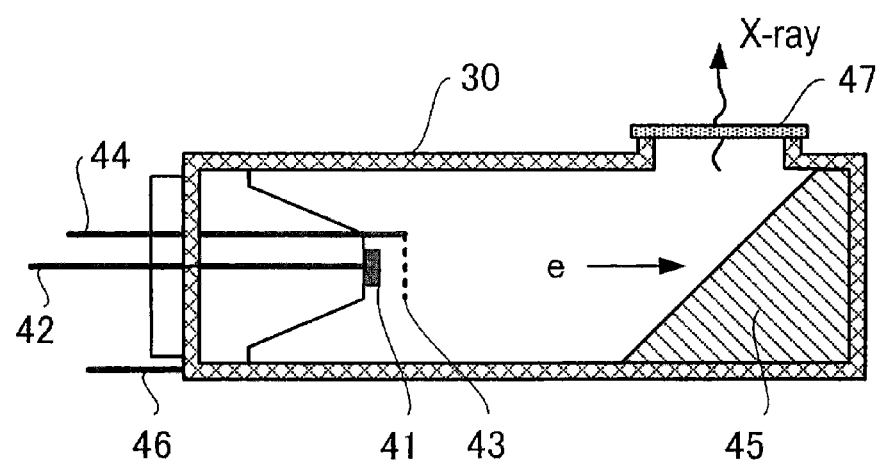
FIG. 4 is a view illustrating an internal configuration of a small X-ray source in the first embodiment.

FIG. 4 is a view illustrating an internal configuration of the small X-ray source 30. The small X-ray source 30 includes a cathode electrode 42 connected to a CNT (Carbon nanotube) cathode 41, a grid electrode 44 connected to a grid 43, an anode electrode 46 connected to a target 45, and an X-ray output port 47. An inside of the small X-ray source 30 is kept in a vacuum state.

In a case where a negative voltage (cut-off voltage) relative to the cathode electrode 42 is applied to the grid electrode 44 when a negative high voltage is applied to the cathode electrode 42, electron emission from the CNT cathode 41 can be prevented. When a voltage at the grid electrode 44 is made equal to that at the cathode electrode 42, electrons are emitted from the CNT cathode 41 and collide with the target 45 connected to a ground potential. As a result, an X-ray is generated from the target 45, allowing the X-ray to be emitted from the X-ray output port 47.

The reason that the small X-ray source 30 is provided with the grid 43 and grid electrode 44 is to apply a high voltage to the plurality of small X-ray sources 30 arranged in the multi-output X-ray source section 10 for preparation of X-ray irradiation and to individually control the voltage to be applied to the grid electrode 44 in accordance with an X-ray irradiation timing for switching a generation position of the X-ray. The high voltage application to each of the small X-ray sources 30 is carried out by a not illustrated high voltage power supply.

In a case where the small X-ray source is not provided with the grid 43, an X-ray high voltage power supply may be provided in each of the small X-ray sources 30 for individual control of the high voltage generation timing. Alternatively, a single common X-ray high voltage power supply may be used to selectively supply a high voltage to the small X-ray sources 30.

The X-ray detection section 11 two-dimensionally detects the X-ray transmitted through the subject P to thereby obtain a transmission image of the subject P. As the X-ray detection section 11, a planar X-ray detector such as an FPD (Flat Panel Detector) is used.

Figure 5:
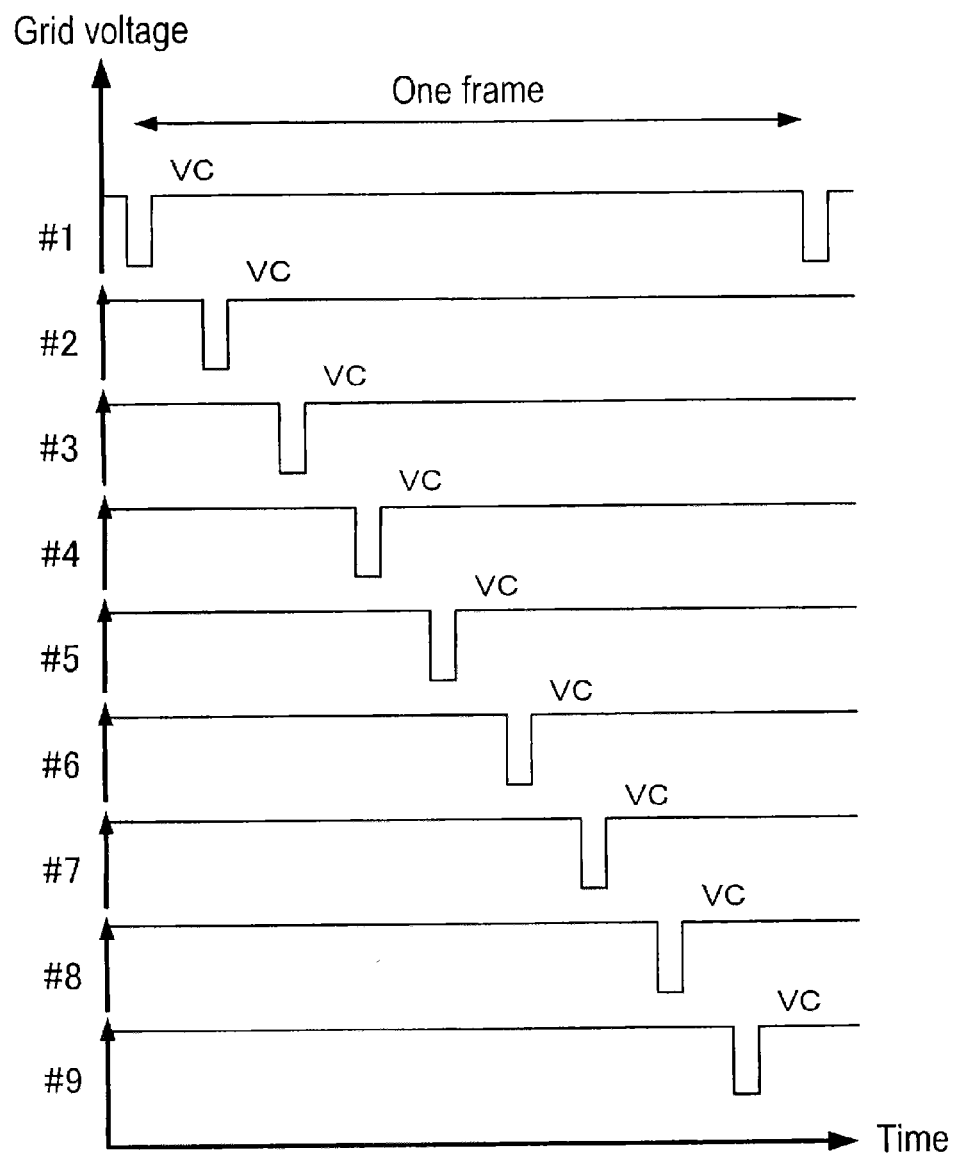
FIG. 5 is a view illustrating an X-ray source switching timing signal in the first embodiment.

The timing controller 12 controls an X-ray generation timing for switching the small X-ray sources 30 constituting the multi-output X-ray source section 10 to thereby sequentially switch the X-ray generation position for scanning and control an image data collection timing at which the image acquisition section 13 collects image data from the X-ray detection section 11. FIG. 5 illustrates an X-ray source switching timing signal output from the timing controller 12 in one frame of an image. In the example of FIG. 5, the small X-ray sources 30#1 to 30#9 of the main row 1 are sequentially scanned such that a grid voltage of each of the small X-ray sources 30#1 to 30#9 is lower than a cathode potential VC to change the X-ray generation position from the X-ray output ports M1 to M9 of FIG. 2. When it is necessary to obtain a video image of 30 frames per second, the switching timing signal for one frame of the image is repeated at a rate of 30 frames per second.

The switching order of the small X-ray sources 30 is not necessarily limited to the above order (ascending order from #1 to #9). For example, small X-ray sources 30 of odd numbers are scanned first, and then those of even numbers (#1→#3→#5→#7→#9→#2→#4→#6→#8). Particularly, in a case where significance is placed on a resolution or video image performance of the transmission image as viewed in front of the subject, scanning of the peripheral small X-ray sources 30 (#1, #2, #8, and #9) are skipped in some frames.

The image acquisition section 13 acquires the transmission image of the subject P corresponding to the small X-ray source 30 switched in synchronization with the X-ray source switching timing signal of the timing controller 12.

Figure 6:
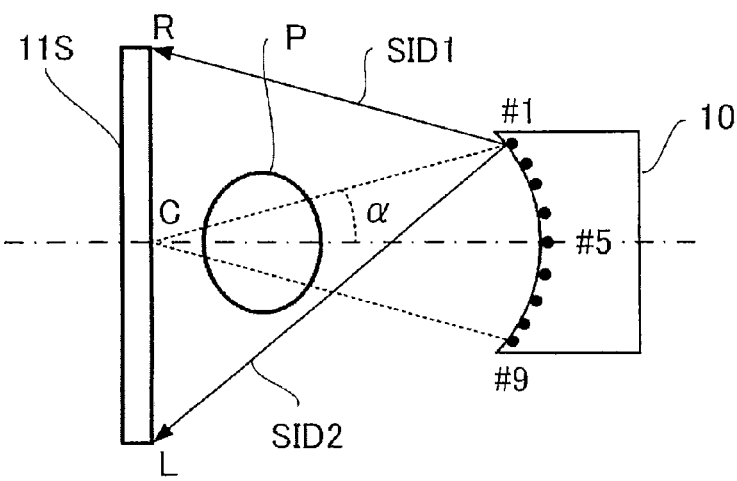
FIG. 6 is an explanatory view of correction of distortion in an azimuth direction in the first embodiment.

The distortion correction section 14 corrects distortion of the transmission image acquired by the image acquisition section 13. FIG. 6 is an explanatory view of correction of distortion in an azimuth direction (as viewed from above the X-ray diagnostic apparatus). The X-ray emitted from the small X-ray source 30#1 spreads as denoted by arrows. In a case where the X-ray detection section 11 is composed of a planar X-ray detector 11S such as a FPD (Flat Panel Detector), a distance SID1 between a point R at a top portion (rightmost portion, from an observer's position) of the planar X-ray detector 11S and small X-ray source 30#1 differs from a distance SID2 between a point L at a bottom portion (leftmost portion, from the observer's position) of the planar X-ray detector 11S and small X-ray source 30#1. A magnification difference caused due to the difference between the SIDs on a surface of the planar X-ray detector is observed as image distortion. Thus, the distortion correction section 14 adjusts a magnification on the surface based on, e.g., a magnification of the SID passing through a center point C to correct the image distortion of the transmission image in the azimuth direction.

Preferably, an arrangement surface of the X-ray output ports of the multi-output X-ray source section 10 is substantially a circular arc as viewed from above such that all the small X-ray sources 30 have the same distance from the center point C of the planar X-ray detector 11S. If the arrangement surface of the X-ray output ports is not the circular arc, the magnification difference calculated from a difference in the SID distance between each of the small X-ray sources 30#1 to 30#9 and center point C is corrected so as to make the magnifications of the transmission images based on the respective small X-ray sources equal to each other.

Image data processed by the distortion correction section 14 is displayed in the stereoscopic image display section 16 as a plurality of images with different disparities and recorded in the image recording section 15. An angle α formed by a line connecting the small X-ray source 30#1, center point C of the planar X-ray detector 11S, and small X-ray source 30#5 illustrated in FIG. 6 represents a maximum parallax angle with respect to a center line denoted by a dashed dotted line in the azimuth direction. Thus, even when a line of sight is moved by up to ±α in the azimuth direction, a stereoscopic perspective image can be obtained.

Figure 7:
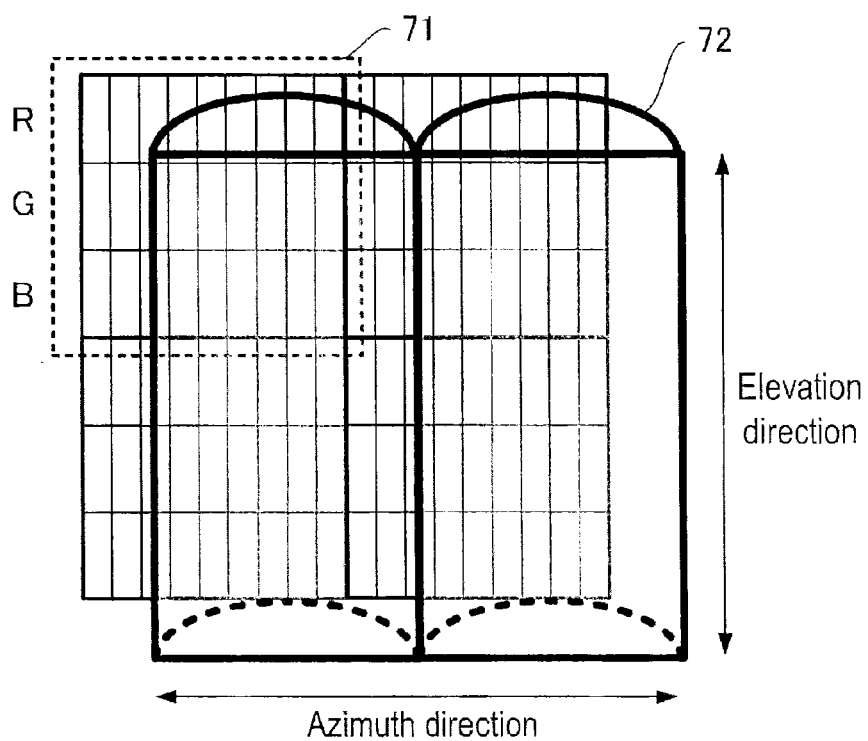
FIG. 7 is a configuration view of a liquid crystal panel in the first embodiment.

The stereoscopic image display section 16 employed in the present embodiment uses a liquid crystal panel that outputs a plurality of images with different disparities so as to allow an observer to observe the stereoscopic perspective image of the subject P without glasses. FIG. 7 is a view illustrating, in an enlarged manner, a configuration of the liquid crystal panel corresponding to four pixels. One pixel 71 of the liquid crystal panel includes 27 sub-pixels, which are divided into three sub-pixel groups of R (red), G (green), and B (blue) each including nine sub-pixels arranged in the azimuth direction. A lenticular sheet 72 is disposed in front of the liquid crystal panel. A horizontal width (azimuth direction width) of one lens of the lenticular sheet 72 is substantially equal to a horizontal width of the one pixel 71. This configuration allows light to be emitted in nine directions from a surface of the liquid crystal panel. Images of the nine sub-pixels arranged in the azimuth direction correspond to the transmission images emitted from the small X-ray sources 30#1 to 30#9 (main row 1) of the multi-output X-ray source section 10. The observer can observe in real time the stereoscopic perspective view only by turning his or her line of sight to a target direction of the subject P.

In the present embodiment, there has been described stereoscopic perspective image generation in which the observer's line of sight are turned in the azimuth direction with only the small X-ray sources of the main row 1 switched. An embodiment in which the small X-ray sources of the sub rows 2 and 3 are used will be described later.

As described above, according to the configuration of the first embodiment, the observer (operator) standing in front of the stereoscopic image display section 16 can observe the stereoscopic perspective image of the subject P. When the observer wants to observe the stereoscopic transmission of the subject P from a position different in the azimuth direction, only turning his or her line of sight to a target part in the azimuth direction allows real time observation of the stereoscopic perspective image of the target position in the form of a video image.

Further, a three dimensional image in the X-ray diagnostic apparatus such as the X-ray CT apparatus or digital tomosynthesis system is obtained by reconstructing a 3D image from a plurality of 2D images; however, in the X-ray diagnostic apparatus of the present embodiment, the image reconstruction need not be performed. Thus, the X-ray diagnostic apparatus of the present embodiment need not necessarily be powerful in computation. By displaying a plurality of transmission images with different lines of sight, a transmission image with stereoscopic effect and a sense of depth can be obtained in real time in the observer's head.

Second Embodiment

Figure 8:
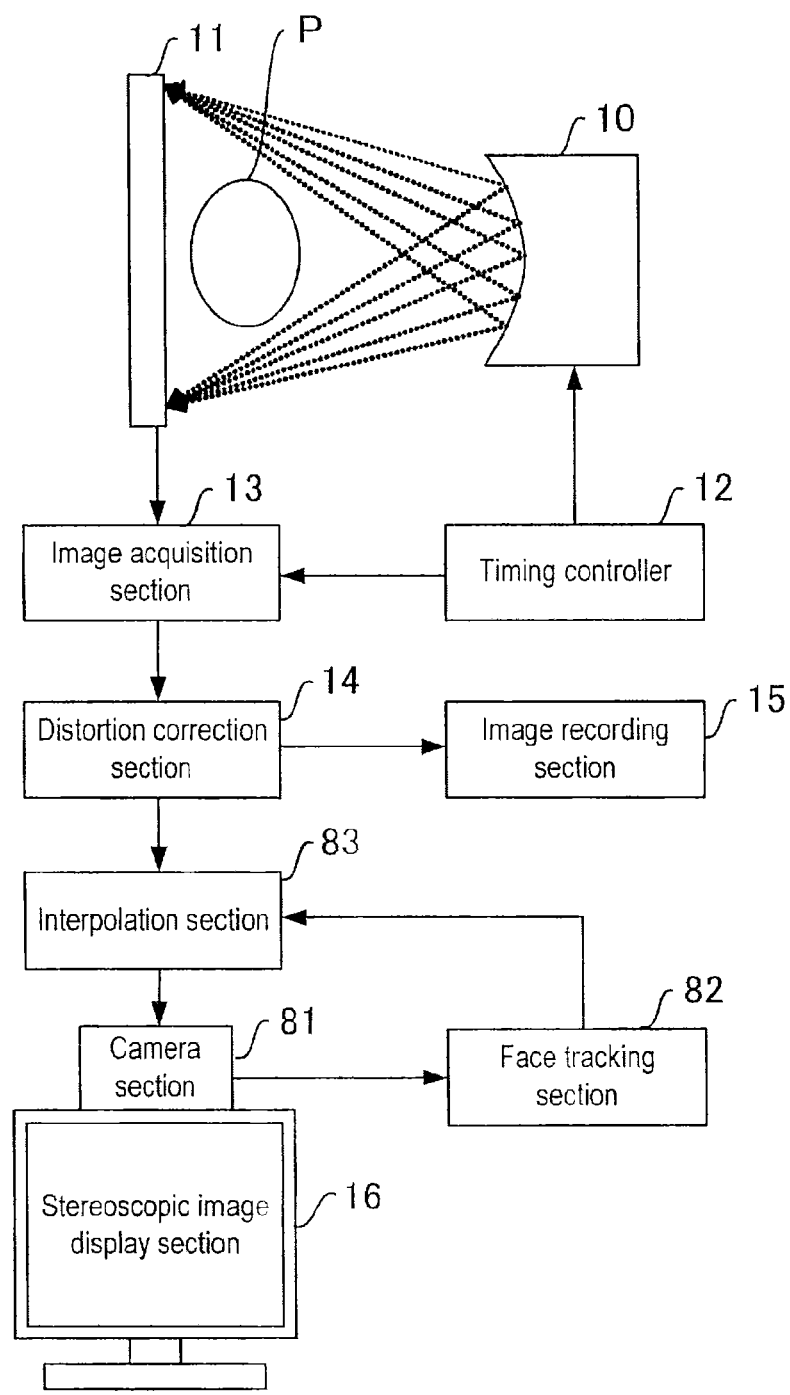
FIG. 8 is a block configuration diagram of an X-ray diagnostic apparatus in a second embodiment.

Next, an embodiment in which the stereoscopic perspective image can be observed when the observer turns his or her line of sight not only in the azimuth direction (first embodiment) but also in an elevation direction will be described. FIG. 8 is a block configuration diagram of an X-ray diagnostic apparatus according to the present embodiment. In addition to the components illustrated in FIG. 1, the X-ray diagnostic apparatus of the present embodiment includes camera sections 81, a face tracking section 82, and an interpolation section 83.

The camera sections 81 are preferably disposed at positions above and below the stereoscopic image display section 16 so as to capture the observation position (line-of-sight position) of the observer. The camera sections 18 are disposed symmetric with respect to a screen of the stereoscopic image display section 16, thereby allowing an angle of the line of sight with respect to a center of the screen to be calculated. The camera section 81 may be realized by an image sensor that captures a visible light in normal circumstances; however, in a case where illumination of an observation room needs to be reduced for medical purposes, an infrared image sensor may be used in the camera section 81.

The face tracking section 82 recognizes a face of the observer captured by the camera sections 81 to recognize motion of his or her line of sight. The face tracking section 82 tracks the motion of the observer's line of sight to calculate the elevation angle of his or her line of sight such that a transmission image corresponding to the observer's eyes always enters his or her eyes.

The interpolation section 83 uses the elevation angle of the observer's light of sight captured by the face tracking section 82 to generate an interpolated image expected to be observed at the elevation angle.

The timing controller 12 scans, in addition to the small X-ray sources of the main row 1, the small X-ray sources of the sub rows 2 and 3. As to the switching timing signal, the number of the small X-ray sources to be switched is different from that in the first embodiment (FIG. 5); however, the output timing thereof is basically the same.

Figure 9:
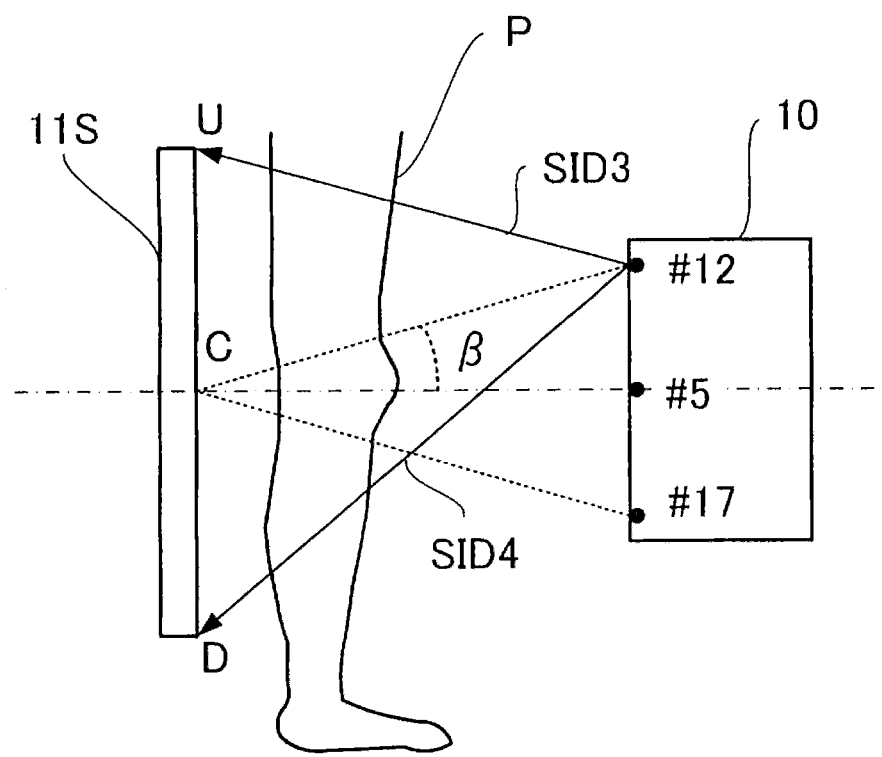
FIG. 9 is an explanatory view of the distortion correction in an elevation direction in the second embodiment.

FIG. 9 is an explanatory view of the distortion correction in the elevation direction, as viewed from a side of the X-ray diagnosis apparatus. A description will be made taking a case where a knee of the subject P in a standing position is observed and diagnosed. The distortion correction section 14 performs the distortion correction of the transmission image acquired by the image acquisition section 13 in the elevation direction, in addition to the distortion correction thereof in the azimuth direction. The X-ray emitted from the small X-ray source 30#12 spreads as denoted by arrows. A distance SID3 between a point U at the top portion of the planar X-ray detector 11S and small X-ray source 30#12 differs from a distance SID4 between a point D at the bottom portion of the planar X-ray detector 11S and small X-ray source 30#12. A magnification difference is caused due to the difference in the SID between the X-ray generation position (small X-ray source 30) and planar X-ray detector 11S on a surface of the planar X-ray detector, thereby causing the image distortion. Thus, the distortion correction section 14 adjusts a magnification on the detector surface based on, e.g., a magnification of the SID passing through the center point C to correct the image distortion of the transmission image in the elevation direction.

Preferably, the arrangement surface of the X-ray output ports of the multi-output X-ray source section 10 is substantially a circular arc as viewed from side such that all the small X-ray sources 30 have the same distance from the center point C of the planar X-ray detector 11S. If the arrangement surface is not the circular arc as illustrated in FIG. 9, the magnification difference calculated from a difference in the SID distance between each of the small X-ray sources 30#12, 30#5, and 30#17 and center point C is corrected so as to make the magnifications of the transmission images based on the respective small X-ray sources equal to each other. Then, the above distortion correction is performed also for the azimuth direction. A slit or the like may be formed in each of the X-ray output ports so as to make the X-ray irradiation direction coincide with the center point C of the X-ray detection section 11.

Figure 10A:
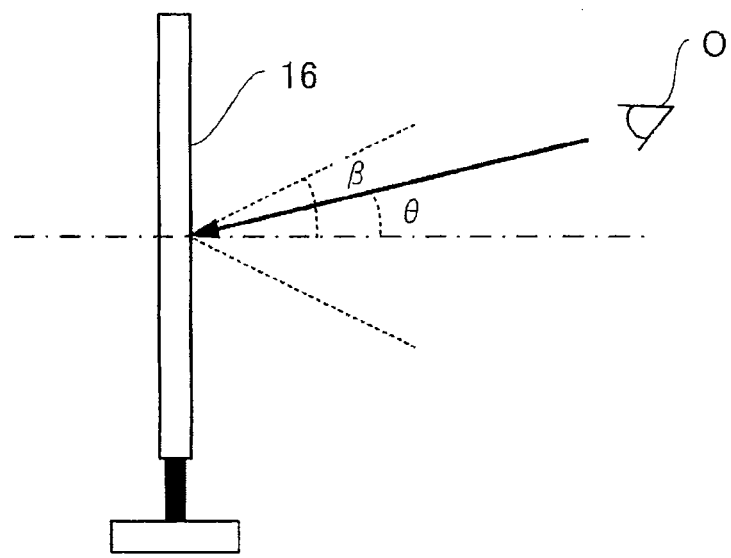
FIG. 10A is an explanatory view of interpolation processing in the second embodiment.
Figure 10B:
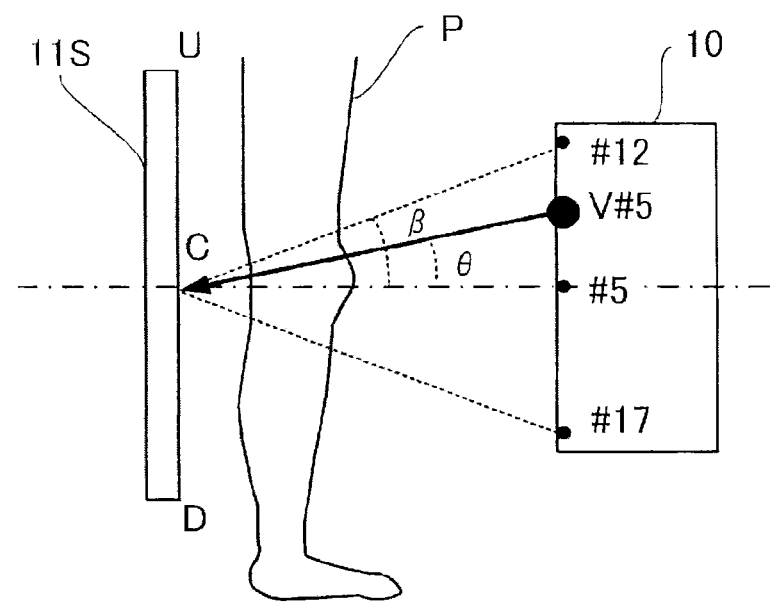
FIG. 10B is an explanatory view of the interpolation processing in the second embodiment.

FIGS. 10A and 10B are explanatory views of interpolation processing to be performed in the interpolation section 83. FIG. 10A is a view for explaining the elevation angle between the observer's line of sight and stereoscopic image display section 16, and FIG. 10B is a view for explaining setting of a virtual X-ray source on the multi-output X-ray source section 10.

The following describes a case where the observer's line of sight O is inclined upward at an angle θ with respect to the center line as illustrated in FIG. 10A. In this case, as illustrated in FIG. 10B, a virtual X-ray source V corresponding to the angle θ is set on the multi-output X-ray source section 10. In the illustrated example, it is assumed that the observer's line of sight passes through a center of the subject P in the azimuth direction and, thus, a virtual X-ray source V#5 is set between the small X-ray source 30#5 of the main row 1 and small X-ray source 30#12 of the sub row 2.

Then, a transmission image of the subject P based on X-ray irradiation from the virtual X-ray source V#5 is calculated. At this time, interpolation processing is performed using the transmission images based on X-ray irradiation from the small X-ray source 30#5 and small X-ray source 30#12 to generate an interpolated image.

The interpolated image is generated in the same manner for each of the small X-ray sources included in the main row 1 other than the small X-ray source 30#5. If the number of the small X-ray sources of the sub row is smaller than that of the main row, interpolation is performed in the elevation angle after interpolated images in the azimuth direction are generated by using the transmission images based on the adjacent small X-ray sources included in the sub row so as to make the number of the transmission images based on the sub rows and those based on the main row coincide with each other.

The interpolated images expected to be obtained when the subject P is irradiated with X-rays emitted from virtual X-ray sources V#1 to V#9 are calculated in this manner, and the calculated interpolated images are input to the stereoscopic image display section 16. As a result, even when the observer moves his or her line of sight in the elevation direction, he or she can observe the stereoscopic perspective image of the subject P tracking the motion of the line of sight. At this time, even the observer moves his or her line of sight also in the azimuth direction, he or she can observe the stereoscopic perspective image tracking the motion of the line of sight in the elevation direction since the interpolated images with nine disparities have been input to the stereoscopic image display section 16.

As described above, according to the configuration of the second embodiment, even when the observer (operator) standing in front of the stereoscopic image display section 16 moves his or her line of sight in both azimuth and elevation directions, he or she can observe in real time the stereoscopic perspective image of the subject P. In addition, in the X-ray CT apparatus, etc., the stereoscopic perspective image of the subject P in a standing position can be observed.

Third Embodiment

In the first and second embodiments, nine transmission images with different disparities are input to the stereoscopic image display section 16. However, in order to obtain the stereoscopic perspective image, it is only necessary to allow two transmission images corresponding to the observer's left and right eyes (binocular parallax) to enter his or her eyes while tracking the motion thereof. The more the number of the transmission images with different disparities to be displayed, the more the pixels corresponding to the transmission images need to be used, and the lower a resolution of a liquid crystal monitor of the stereoscopic image display section 16. This may easily lead to erroneous interpretation.

Figure 11:
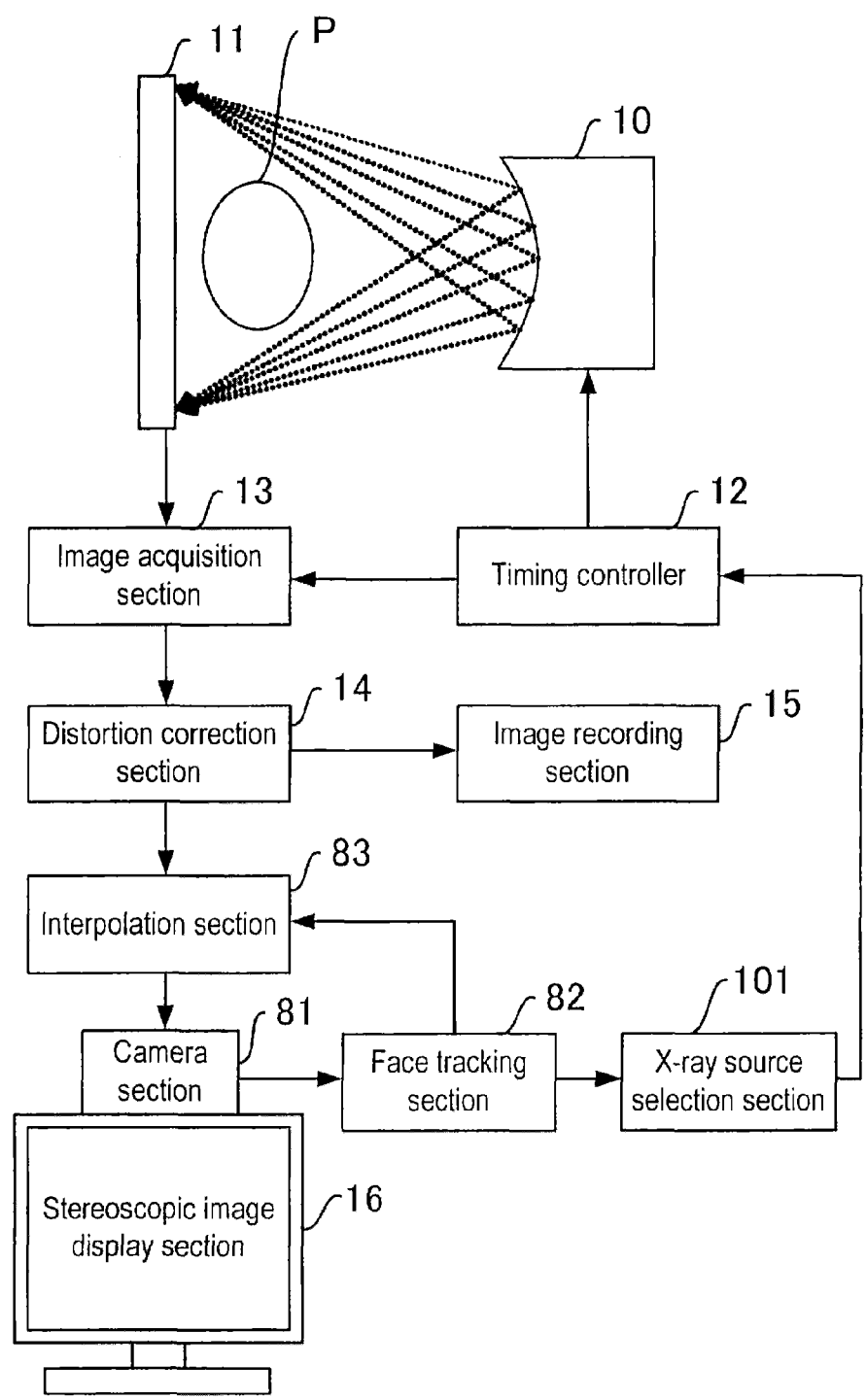
FIG. 11 is a block diagram of an X-ray diagnostic apparatus in a third embodiment.

In the present embodiment, two transmission images corresponding to the left and right eyes are used for an increase in the resolution and video image performance of a medical image. In addition, the X-ray diagnostic apparatus according to the present embodiment can be configured such that unnecessary small X-ray sources do not generate the X-ray, allowing a reduction in the exposure dose. FIG. 11 is a block diagram of an X-ray diagnostic apparatus in the present embodiment. In addition to the components illustrated in FIG. 8, the X-ray diagnostic apparatus of the present embodiment includes an X-ray source selection section 101.

The face tracking section 82 detects in real time an observation direction of the observer and inputs angle information in the elevation and azimuth directions of the line of sight thereof to the X-ray source selection section 101. The X-ray source selection section 101 selects a minimum necessary number of the small X-ray sources.

Figure 12:
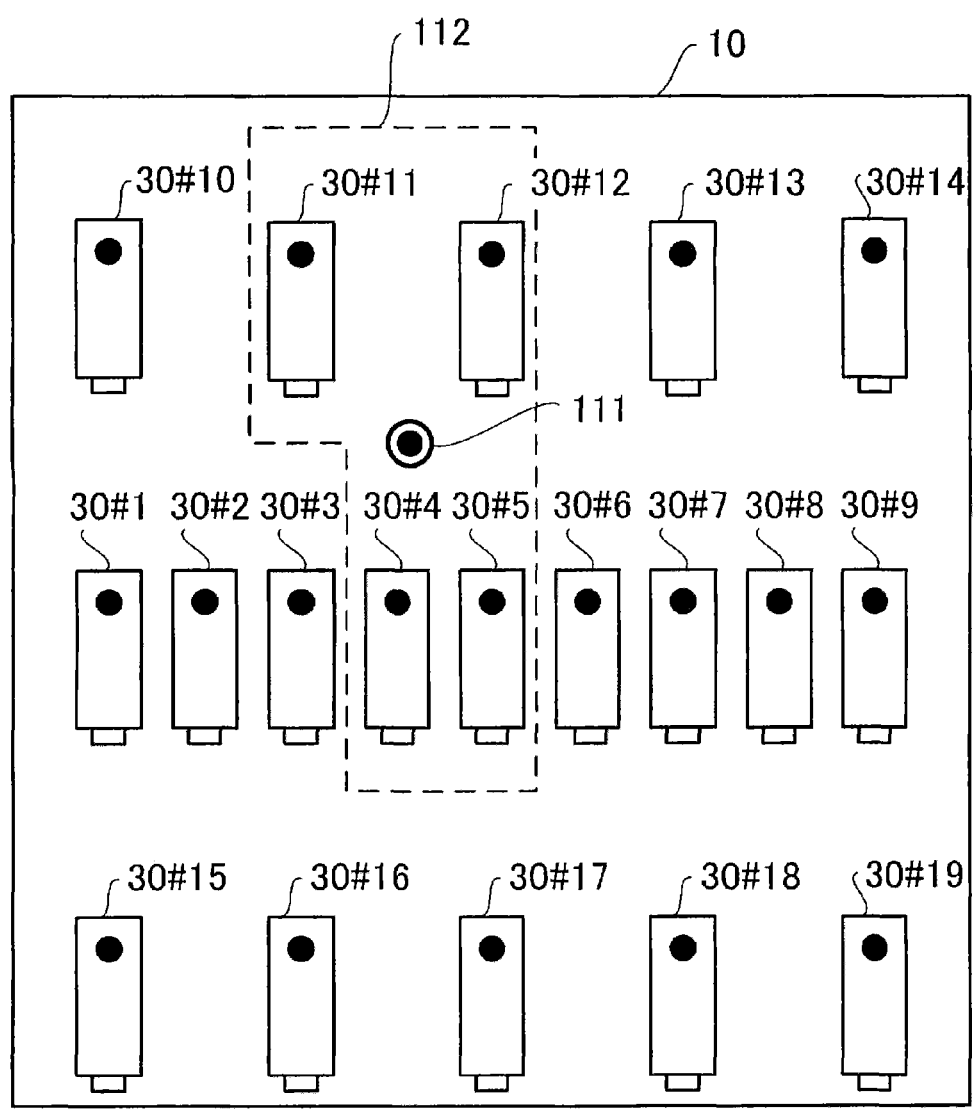
FIG. 12 illustrates an example of selection of the small X-ray sources in the third embodiment.

FIG. 12 illustrates an example of selection of the small X-ray sources. The X-ray source selection section 101 calculates a virtual X-ray generation position corresponding to the elevation and azimuth directions of the observer's line of sight. The calculated X-ray generation position is denoted by a double circle and referred to as "virtual X-ray source 111". As denoted by a dashed frame 112, in order to obtain the virtual X-ray source 111, at least two small X-ray sources adjacent to the virtual X-ray source 111 are selected from the main row and sub row, respectively. In the illustrated example, the small X-ray sources 30#4, 30#5, 30#11, and 30#12 are selected. Then, information relating to the selected small X-ray sources is given to the timing controller 12.

The timing controller 12 generates an X-ray source timing signal for causing only the selected small X-ray sources to generate the X-ray in series. The image acquisition section 13 acquires the transmission images of the subject P corresponding to the small X-ray sources selected at the timing specified by the X-ray source timing signal.

After the distortion correction for each of the transmission images, the interpolation section 83 calculates a transmission image corresponding to the virtual X-ray source 111 by interpolation. At this time, the interpolation section 83 calculates two images corresponding to the disparity of the observer's left and right eyes by the interpolation.

The calculated interpolated images are input to the stereoscopic image display section 16, thereby allowing the stereoscopic perspective image tracking the observer's line of sight to be observed. That is, the observer can always observe the stereoscopic perspective image corresponding to his or her line of sight even when moving his or her eyes.

As described above, according to the third embodiment, only a minimum necessary number of the small X-ray sources are selected for generation of the two transmission images corresponding to the left and right eyes to avoid use of the small X-ray sources other than the selected ones. This can achieve a reduction in the exposed dose and can prevent the resolution of the stereoscopic image display section 16 from being lowered. In addition, the number of the small X-ray sources to be switched in one frame is reduced, thereby allowing the number of frames to be increased. This can enhance the video image performance in observing a fast moving organ, such as heart.

Further, due to use of the two images corresponding to the left and right eyes, the present embodiment can employ a stereoscopic image display device of a type on which the observer observes a stereoscopic image by wearing 3D glasses.

Fourth Embodiment

In the embodiments described above, there has been described an apparatus by which the stereoscopic perspective image of the subject can be observed in real time in accordance with the observer's line of sight position. In the present embodiment, display processing of the stereoscopic perspective image based on recorded transmission images will be described. This embodiment is suitably used for observation to be made from a line of sight position different from that at a diagnosis time, second diagnosis by another doctor, or explanation to a patient.

Figure 13:
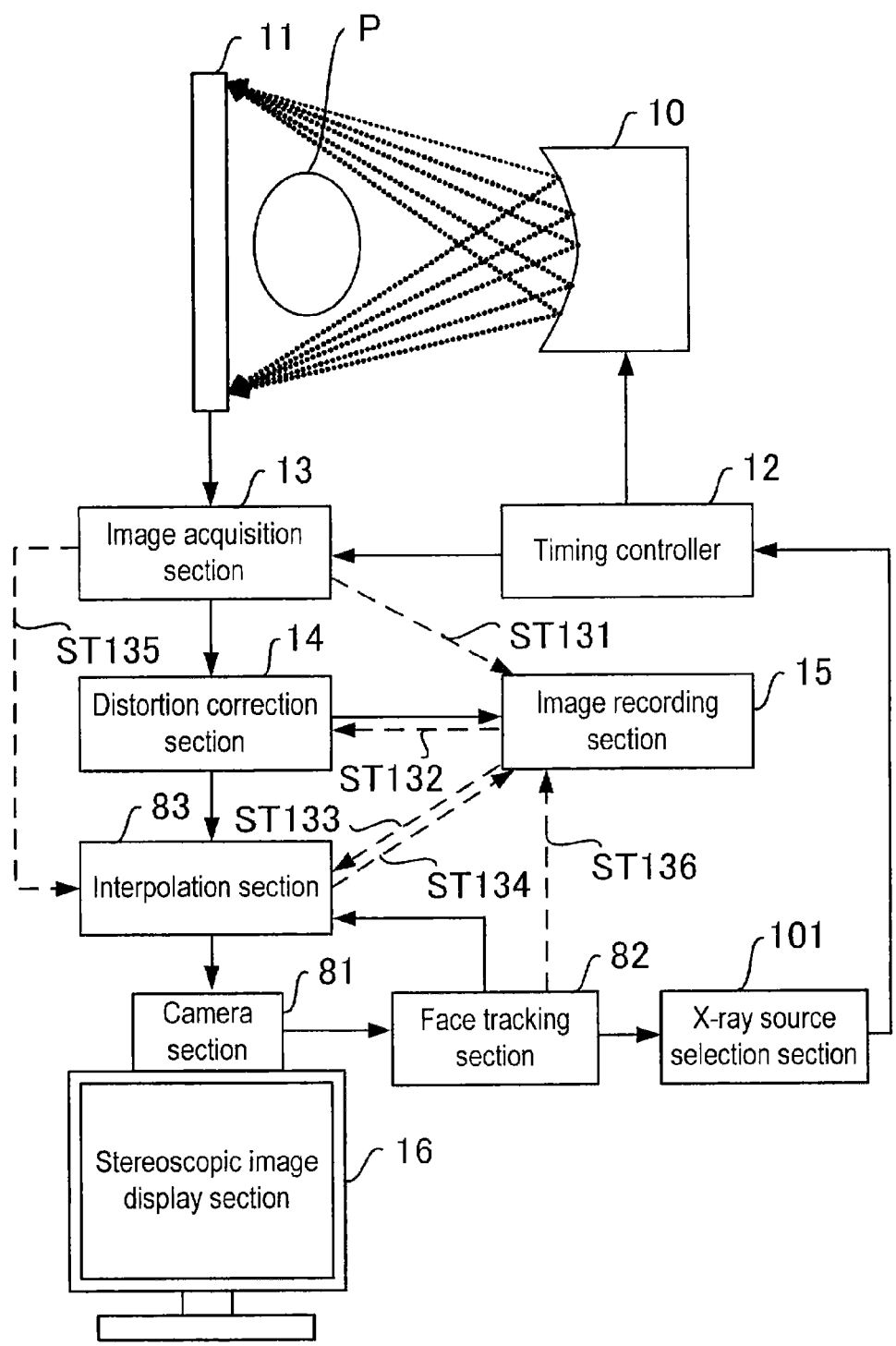
FIG. 13 is a block diagram of an X-ray diagnostic apparatus in a fourth embodiment.

Various image data to be recorded in the image recording section 15 of the present embodiment will be described. FIG. 13 is a block configuration diagram of an X-ray diagnostic apparatus in the present embodiment. In this diagram, flows of the image data are added to the components illustrated in FIG. 11.

Flows of the image data in steps ST131 to ST136 denoted by dashed arrows will be described.

Step ST131 is a processing flow that directly stored the transmission image of the subject P acquired by the image acquisition section 13 in the image recording section 15 without applying the distortion correction thereto. Step ST132 is a processing flow in which the distortion correction section 14 reads out image data stored in the image recording section 15 and applies the distortion correction to the read out image data.

When, as described above, the transmission image of the subject P acquired by the image acquisition section 13 is directly stored without any processing, it is possible to apply various image processing such as the distortion correction processing and contrast correction to necessary image data after radiography of the subject P and display the resultant image data on the stereoscopic image display section 16. The resultant image data may be stored again in the image recording section 15.

Step ST133 is a processing flow in which the interpolation section reads out the image data stored in the image recording section 15 and performs the interpolation processing using the read out image data by the interpolation section 83. That is, after radiography of the subject P, image data required for diagnosis can be read out from among the image data stored in the image recording section 15 for application of the interpolation processing and display of the interpolated image data on the stereoscopic image display section 16. Further, as denoted by a dashed arrow of ST134, the interpolated image data may be stored again in the image recording section 15.

For example, radiography condition information such as the azimuth angle, elevation angle, and the like is added to property of the interpolated image data, and the observer observes the stereoscopic image display section from a direction specified by the radiography condition information, whereby the stereoscopic perspective image can be observed by the observer.

Step ST135 is a processing flow in which the image data acquired by the image acquisition section 13 is directly input to the interpolation section 83 without passing through the image distortion correction section 14. This processing flow may be applied when the correction of the distortion caused due to the magnification difference in the SID. Further, for example, image data obtained by performing the interpolation processing using the transmission images based on the X-ray sources of the sub row in a predetermined azimuth direction may be subjected to the distortion correction as needed in the distortion correction section 14 after being recorded once in the image recording section 15 according to the dashed arrow of step ST134. The processing flows of step ST131 to ST135 are also added to FIGS. 1 and 8.

Step ST136 is a processing flow that selects desired image data from among the various image data stored in the image recording section 15 according to the line of sight position detected by the face tracking section 82. The processing flow of step ST136 is also added to FIG. 8.

Since storage and readout of the various data can be performed in the above manner, observation in a direction different from that at the diagnosis time can be made possible. Further, when a long time is taken for the diagnosis at the X-ray irradiation time, the exposure dose may increase; however, by recording the image data once in the image recording section 15, a stereoscopic perspective image can be observed after the radiography from a desired line of sight position without having to worry about the elapsed time. This can prevent erroneous diagnosis and reduce the exposure dose.

In addition, since the recorded data can be transportable, the stereoscopic perspective image can be reproduced not only in the X-ray diagnosis apparatus but also in a personal computer provided with the stereoscopic image display section. Further, functions of the distortion correction section 14, interpolation section 83, and the like may be implemented in the personal computer. The image data to be displayed on the stereoscopic image display section includes various image data for stereoscopic display, such as image data which is composed of a plurality of images with different disparities so as to allow the observer to observe the stereoscopic perspective image without glasses or image data composed of two images corresponding to the left and right eyes, which is obtained by using a liquid crystal shutter.

As described above, according to the fourth embodiment, recording/reproduction of the raw transmission data of the subject and image data that has been subjected to various processing for stereoscopic perspective display can be made possible. This allows the stereoscopic perspective view to be displayed from a line of sight different from that at the diagnosis time.

According to the embodiments described above, absence of mechanical rotation and a movement mechanism allows high-speed switching of the transmission images, thereby allowing the stereoscopic perspective image of a fast moving organ, such as heart to be observed in the form of a video image. In addition, the three dimensional image can be obtained in the observer's head (i.e., image reconstruction need not be performed), thereby eliminating the need to use a computer having high computing power. Further, in the case of the X-ray CT apparatus and the like, diagnosis is performed in a state where a patient is lying on a bed; on the other hand, in the case of the X-ray diagnosis apparatus of the present embodiments, observation can be possible even in a state where the patient is in a standing position. This allows an organ (especially, knee joint) in a loaded condition to be observed in the form of a video image.

As a matter of course, it is possible to apply a tomographic image synthesis technology to the transmission images acquired using the multi-output X-ray source section of the present embodiments to reconstruct the three dimensional image and display it on a commonly used monitor. Also in this case, observation can be made in the form of a video image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and sprit of the inventions.

What is claimed is:

1. An X-ray diagnosis apparatus comprising:
a main row X-ray source group including a first plurality of X-ray sources arranged in an azimuth direction;
a sub row X-ray source group which is arranged at a position shifted in an elevation direction from the main row X-ray source group, wherein the sub row X-ray source group includes a second plurality of X-ray sources arranged in the azimuth direction;
an X-ray detection section disposed opposite to the X-ray sources;
a timing controller that controls a switching timing of the X-ray sources and an X-ray generation position;
an image acquisition section that acquires output image data from the X-ray detection section in synchronization with the switching timing;
a face tracking section that detects a line of sight position of an observer with respect to a stereoscopic image display section;
an interpolation section that generates a plurality of images with different disparities corresponding to the line of sight position by performing interpolation using the output image data from the X-ray detection section corresponding to the X-ray sources included in the main row X-ray source group and sub row X-ray source group; and
the stereoscopic image display section that displays the plurality of images having different disparities, wherein
the stereoscopic image display section is a liquid crystal panel capable of emitting light in different directions from a panel surface, wherein the liquid crystal panel emits the plurality of images having different disparities in respective ones of the different directions,
a number of the X-ray sources of the sub row X-ray source group is less than a number of the X-ray sources of the main row X-ray source group, and
the interpolation section generates interpolated images in the azimuth direction by using a portion of the output image data corresponding to the X-ray sources of the sub row X-ray source group, and thereafter the interpolation section generates the plurality of images by performing interpolation in the elevation direction using the interpolated images and the output image data corresponding to the X-ray sources of the main row X-ray source group and sub row X-ray source group.

2. The X-ray diagnosis apparatus according to claim 1, further comprising a distortion correction section that corrects image distortion of the output image data from the X-ray detection section.

3. The X-ray diagnosis apparatus according to claim 2, further comprising an image recording section that records therein the image data output from one of the image acquisition section and distortion correction section.

4. The X-ray diagnosis apparatus according to claim 2, further comprising an image recording section that records therein the image data output from one of the image acquisition section, distortion correction section, and interpolation section.

5. The X-ray diagnosis apparatus according to claim 4, wherein
the image recording section stores therein the plurality of images with different disparities generated by the interpolation section.

6. The X-ray diagnosis apparatus according to claim 1, wherein
the interpolation section generates two images having different disparities corresponding to left and right eyes of the observer in the line of sight position thereof detected by the face tracking section by performing interpolation using output images of the X-ray detection section corresponding to the X-ray sources adjacent to the line of sight position.

7. The X-ray diagnosis apparatus according to claim 6, further comprising an X-ray source selection section that selects the X-ray sources adjacent to the line of sight position for switching.

8. The X-ray diagnosis apparatus according to claim 7, further comprising:
a distortion correction section that corrects image distortion of the output image data from the X-ray detection section; and
an image recording section that records therein the image data output from one of the image acquisition section, distortion correction section, and interpolation section.

9. The X-ray diagnosis apparatus according to claim 8, wherein
the image recording section stores therein image data of the X-ray sources selected by the X-ray source selection section.

10. The X-ray diagnosis apparatus according to claim 9, wherein
the image recording section stores the two images with different disparities generated by the interpolation section.

11. The X-ray diagnosis apparatus according to claim 3, wherein
the distortion correction section corrects image distortion of the recorded image data.

12. The X-ray diagnosis apparatus according to claim 3, wherein
the interpolation section generates a plurality of images with different disparities by performing interpolation using the image data acquired from one of the image recording section and distortion correction section.

* * * * *